United States Patent [19]

Brigandat et al.

[11] Patent Number: 4,937,383
[45] Date of Patent: Jun. 26, 1990

[54] PROCESS FOR MANUFACTURING AMINES FROM OLEFINS

[75] Inventors: Yves Brigandat, Vaulx-en-Velin; Jacques Kervennal, Lyons, both of France

[73] Assignee: Atochem, Paris la Defense, France

[21] Appl. No.: 246,985

[22] Filed: Sep. 20, 1988

[30] Foreign Application Priority Data

Oct. 2, 1987 [FR] France ................. 87 13873

[51] Int. Cl.$^5$ .............................................. C07C 85/06
[52] U.S. Cl. ..................... 564/479; 564/485; 564/480
[58] Field of Search ................. 564/479, 480, 485

[56] References Cited

U.S. PATENT DOCUMENTS

| | | | |
|---|---|---|---|
| 4,314,083 | 2/1982 | Ford et al. | 564/479 |
| 4,459,191 | 7/1984 | Gardner et al. | 204/157.81 |
| 4,483,747 | 11/1988 | Aruga et al. | 203/92 |

FOREIGN PATENT DOCUMENTS

| | | | |
|---|---|---|---|
| 0039061 | 11/1981 | European Pat. Off. | 564/485 |
| 0200923 | 11/1986 | European Pat. Off. | 564/485 |
| 502737 | 3/1939 | United Kingdom . | |

*Primary Examiner*—Glennon H. Hollrah
*Assistant Examiner*—Mark W. Russell
*Attorney, Agent, or Firm*—Sigalos, Levine & Montgomery

[57] ABSTRACT

A process for the manufacture of amines by reacting at an elevated temperature an olefin selected from a monoolefin, the alcohol corresponding to its hydration, or a mixture of the monoolefin and the alcohol with ammonia or a primary or secondary amine in the presence of a catalyst and a solvent, said catalyst being ammonium sulfate of a double sulfate of ammonium and a transition metal.

10 Claims, 1 Drawing Sheet

PROCESS FOR MANUFACTURING AMINES FROM OLEFINS

BACKGROUND OF THE INVENTION

The invention pertains to a process for manufacturing amines by reacting at a high temperature a monoolefin with ammonia or a primary or secondary amine in the presence of a catalyst.

It is known how to perform such a reaction, for example, using the processes described in European patent application Nos. EP-0,039,061 and EP-0,200,923. The first process consists of working at a temperature ranging between 100° C. and 250° C. in the presence of a catalyst with a base of ruthenium or iron dissolved in a solvent medium. It seems to be suitable only for ethylene and has the disadvantage of not selectively producing a specific amine. The second process consists of working at a temperature ranging preferably between 250° C. and 350° C. in the presence of an ammonium halide as a catalyst. The latter is preferably accompanied by a transition metal-based promotor with no catalytic activity of its own, which may be either a transition metal halide or an ammonium salt of a transition metal oxyacid.

According to U.S. Pat. Nos. 4,459,191 and 4,483,747 an ammonium halide is also suitable for obtaining amines from olefins by liquid-phase photocatalysis.

Thus, the ammonium halides are specifically distinguished in the prior art among the compounds containing a NH4 ammonium group.

SUMMARY OF THE INVENTION

It has now been found that compounds with NH4 groups other than halides are particularly suited to obtaining an amine effectively and selectively from a monoolefin, as well as from the alcohol corresponding to hydration of the olefin or mixtures of an olefin and said alcohol.

The present invention has in fact as its object a process for the manufacturing of an amine by reacting at a high temperature a monoolefin or the alcohol corresponding to its hydration or of a mixture of a monoolefin and the said alcohol with ammonia or a primary or secondary amine in the presence of a catalyst and a solvent, characterized by the fact that the catalyst is ammonium sulfate $(NH_4)_2 SO_4$ or a double sulfate of ammonium and a transition metal.

DETAILED DESCRIPTION

Figure 2:
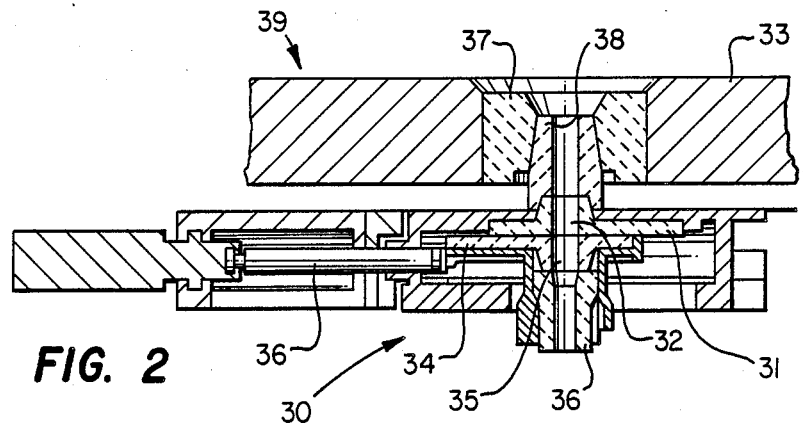

Ammonium sulfate can be used as is, for example, it can be formed from ammonia and sulfuric acid or ammonium acid sulfate.

Double sulfates of ammonium and transition metal that are suitable for the invention are, for example, those of the alum type of the general formula $XNH_4(SO_4)_2 \cdot 12H_2O$, in which X represents the transition metal.

Most generally, the transition metal is selected from among chromium, rhodium, vanadium and iron, with the iron usually being preferred to the others.

The catalyst is used in an amount that is generally such that the catalyst/olefin molar ratio ranges between ca. 0.01 and 0.5.

The $NH_3$ (or primary or secondary amine)/olefin molar ratio usually ranges between 1/1 and 10/1 and is preferably at least equal to 2/1.

The temperature at which the process according to the invention is conducted is at an elevated temperature, generally ranges between ca. 200° C. and 450° C. to ensure sufficiently high conversion of the olefin and selectivity of amine produced.

For an olefin containing four carbon atoms in its molecule, as for example isobutene, the temperature will generally be not greater than ca. 300° C.

The pressure is the autogenous pressure provided by the reaction medium under the conditions selected for execution of the process. In the case of isobutene, for example, it is practically no less than ca. 100 bars absolute.

The olefin and amine which, besides $NH_3$, is called on to react with it are selected among those commonly cited in connected with a process of the type specific to the invention, for example, in European patent application No. EP-0,200,923. Among the monoolefins to which the invention thus applies and which have two to eight carbon atoms in their molecule, those with two to four carbon atoms in their molecule such as isobutene, are preferred.

That which is stated above for the olefin is true for the alcohol corresponding to its hydration as well as for the olefin and the said alcohol in a mixture, for example, for isobutene, tert-butanol or their mixtures.

Ammonia is often selected in preference to an amine for reasons of cost and availability, and for reasons of selectivity and importance of primary amines.

The solvents used can be of the type of those cited in European patent application No. EP-0,200,923, but water, the alcohol corresponding to the hydration of the olefin, or their mixtures are preferred.

The olefin, alcohol, ammonia or amine recoverable in terms of the procedures according to the invention may obviously be profitably recycled.

The length of the procedure according to the invention depends on the selection of the olefin and reaction parameters. It often ranges between ca. a few dozen minutes and about 15 hours, generally between one and ten hours.

The invention will be further described in connection with the following examples which are set forth for purposes of illustration only.

They pertain to isobutene and the amine formed is tert-butylamine

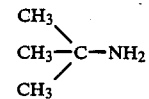

whose value in industry is progressively increasing, particularly in the plant health field.

The conversion of olefin to amine is expressed in number of moles of olefin converted to amine per 100 moles of olefin used.

The amine selectivity is expressed by the ratio of number of olefin moles converted to amine to total of olefin moles converted per 100 moles of olefin used.

When alcohol intervenes, it is blended with the olefin for the determination of conversion and selectivity, with the alcohol and olefin being recyclable.

It has been confirmed that no amine forms in the absence of a catalyst.

EXAMPLE 1

A mixture formed from 90 g (5.3 moles) of anhydrous ammonia, 56 g (1 mole) of isobutene, 20 g (0.15 mole) of ammonium sulfate $(NH_4)_2SO_4$ and 360 g (20 moles) of water is kept at 250° C. for ten hours while agitating in a one-liter stainless-steel autoclave. The pressure is the autogenous pressure.

25.6 (0.35 mole) of tert-butylamine are obtained, corresponding to a 35% conversion of isobutene to amine, in addition to untransformed isobutene and 14.8 g (0.2 mole) of tert-butanol.

EXAMPLE 2

A mixture containing the same quantities of isobutene, ammonia and water as in Example 1 and 6.6 g (0.05 mole) of ammonium sulfate are kept at 240° C. for eight hours while agitating under autogenous pressure in the autoclave described in Example 1.

11 g (0.15 mole) of tert-butylamine are obtained, corresponding to a 15% conversion of isobutene to amine, in addition to untransformed isobutene and 16.3 g (0.22 mole) of tert-butanol.

EXAMPLE 3

Example 2 is repeated, with the difference that the ammonium sulfate amount used is equal to 26.4 g (0.2 mole) and that the mixture is kept at 240° C. for only five hours.

16.8 g (0.23) of tert-butylamine are obtained, corresponding to a 23% isobutene conversion rate, in addition to untransformed isobutene and 14.8 g (0.2 mole) of tert-butanol.

EXAMPLE 4

A mixture formed from 74 g (1 mole) of tert-butanol, 90 g (5.3 moles) of anhydrous ammonia, 40 g (0.3 mole) of ammonium sulfate and 360 g (20 moles) of water is kept while agitating at 240° C. for ten hours under autogenous pressure in the autoclave described in Example 1.

In this manner, 22 g (0.3 mole) of tert-butylamine are obtained; a 30% conversion of tert-butanol to amine, in addition to 32 g (0.57 mole) of isobutene.

EXAMPLE 5

Example 1 is repeated using 28 g (0.5 mole) of isobutene and 37 g (0.5 mole) of tert-butanol.

33.6 g (0.46 mole) of tert-butylamine are obtained; a 46% cumulative conversion of olefin and tert-butanol, in addition to 21.3 g (0.38 mole) of isobutene, while 11.8 g (0.16 mole) of tert-butanol remain.

By way of comparison, the repeating of Example 5 using $NH_4Cl$ instead of $(NH_4)_2SO_4$, in equal molar amount, yields the formation of only 20 g (0.27 mole) of tert-butylamine.

EXAMPLE 6

A mixture formed from 74 g (1 mole) of tert-butanol, 90 g (5.3 moles) of anhydrous ammonia and 9 g (0.07 mole) of ammonium sulfate is kept under agitation for five hours at 240° C. in the autoclave described in Example 1.

7.3 g (0.1 mole) of tert-butylamine and 44.4 g of isobutene form.

EXAMPLE 7

Example 1 is repeated, with the following differences: The double sulfate of ammonium and iron, $NH_4Fe(SO_4)_2$, is used at the rate of 11.3 g (0.05 mole) instead of plain ammonium sulfate, and the residence time at the temperature of 250° C. is five hours instead of ten hours.

14.5 g (0.2 mole) of tert-butylamine are obtained, corresponding to a 20% conversion of olefin to amine, in addition to untransformed isobutene and 15 g (0.2 mole) of tert-butanol.

In all the above examples according to the invention, the formation of oily products was not observed, and the selectivity of the tert-butylamine reaction was always practically equal to 100% or very close to 100% to within the nearest measurement errors.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

What is claimed is:

1. A process for the manufacture of amines by reacting at an elevated temperature an olefin selected from a monoolefin, the alcohol corresponding to its hydration, or a mixture of said monoolefin and the said alcohol with ammonia or a primary or secondary amine in the presence of a catalyst and a solvent, said catalyst being ammonium sulfate or a double sulfate of ammonium and a transition metal.

2. The process of claim 1, wherein the transition metal is selected from chromium, rhodium, vanadium or iron.

3. The process of claim 2, wherein the double sulfate of ammonium and a transition metal is of the alum type.

4. The process of claim 3 wherein the

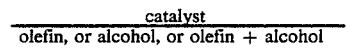

molar ratio ranges between 0.01 and 0.5.

5. The process of claim 4, wherein the

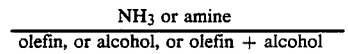

molar ratio ranges between one and ten.

6. The process of claim 5, where the

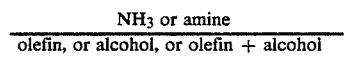

molar ratio is at least equal to 2.

7. The process according to any of claims 1 to 6, wherein the reaction of the olefin with ammonia or primary or secondary amine is performed at a temperature ranging between about 200° C. to 450° C. under autogenous pressure.

8. The process according to any of claims 1 to 6, wherein the solvent is water, or the alcohol corresponding to that obtained when the olefin is hydrated, or mixtures thereof.

9. The process of any one of any of claims 1 to 6 wherein the olefin has 2 to 8 carbon atoms, the reaction is carried out at a temperature of about 200° C. to 450° C. under autogenous pressure, and the solvent is water, or the alcohol corresponding to that obtained when the olefin is hydrated, or mixtures thereof.

10. The process of any one of claims 1 to 6 wherein the olefin is selected from isobutene, tert-butanol, or mixtures thereof.

* * * * *

UNITED STATES PATENT AND TRADEMARK OFFICE
CERTIFICATE OF CORRECTION

PATENT NO. : 4,937,383

DATED : June 26, 1990

INVENTOR(S) : Brigandat, et al

It is certified that error appears in the above-identified patent and that said Letters Patent is hereby corrected as shown below:

Title page, right-hand column, last line, cancel "1 Drawing Sheet" and substitute therefor --No Drawings--.

Figure 1:
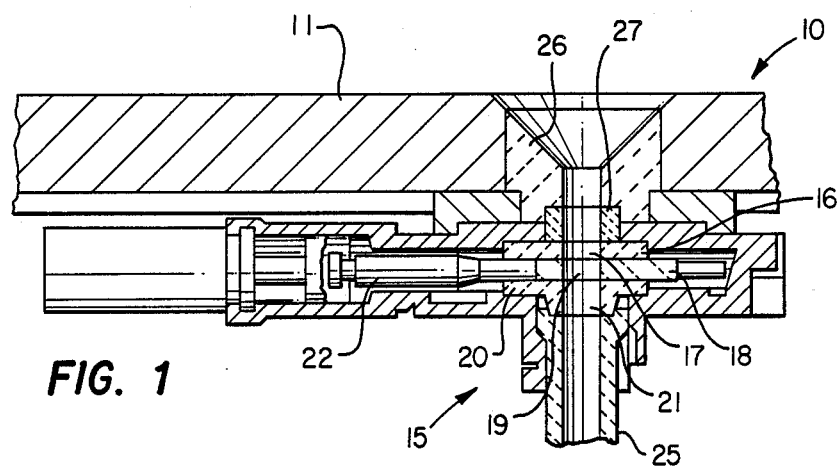
Figure 3:
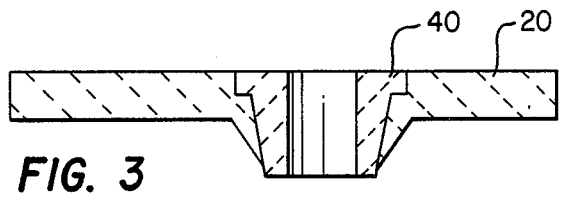

Cancel the single sheet of drawing which contains Figures 1, 2 and 3.

Signed and Sealed this

Twenty-fourth Day of September, 1991

*Attest:*

HARRY F. MANBECK, JR.

*Attesting Officer*  Commissioner of Patents and Trademarks